United States Patent
Raventos et al.

(12)

(10) Patent No.: US 10,843,125 B2
(45) Date of Patent: Nov. 24, 2020

(54) PROCESS FOR THE SEPARATION OF METHANOL FROM GAS MIXTURES

(71) Applicant: L'Air Liquide, Societe Anonyme pour l'Etude et l'Exploitation des Procedes Georges Claude, Paris (FR)

(72) Inventors: Martin Raventos, Frankfurt (DE); Jorg Ott, Frankfurt (DE); Tobias Oelmann, Bad Vilbel (DE); Benjamin Nuri, Oberursel (DE)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 222 days.

(21) Appl. No.: 16/063,508

(22) PCT Filed: Dec. 6, 2016

(86) PCT No.: PCT/EP2016/025170
§ 371 (c)(1),
(2) Date: Jun. 18, 2018

(87) PCT Pub. No.: WO2017/102095
PCT Pub. Date: Jun. 22, 2017

(65) Prior Publication Data
US 2018/0369745 A1    Dec. 27, 2018

(30) Foreign Application Priority Data

Dec. 18, 2015    (EP) ..................................... 15400056

(51) Int. Cl.
*B01D 53/18* (2006.01)
*C07C 29/76* (2006.01)
(Continued)

(52) U.S. Cl.
CPC ......... *B01D 53/185* (2013.01); *B01D 5/0063* (2013.01); *B01D 53/1487* (2013.01);
(Continued)

(58) Field of Classification Search
CPC .............. B01D 5/0063; B01D 53/1487; B01D 53/185; B01D 2252/103; B01D 2256/10;
(Continued)

(56) References Cited

U.S. PATENT DOCUMENTS

| 3,950,369 A | 4/1976 | Gent |
| 4,181,675 A | 1/1980 | Makin et al. |

(Continued)

FOREIGN PATENT DOCUMENTS

| DE | 2934332 A1 | 3/1981 |
| EP | 0009385 A1 | 4/1980 |

(Continued)

OTHER PUBLICATIONS

International Search Report and Written Opinion corresponding to PCT/EP2016/025170 dated Mar. 24, 2017.

*Primary Examiner* — Charles S Bushey
(74) *Attorney, Agent, or Firm* — Justin K. Murray (57) ABSTRACT

With the invention a washing apparatus and a process for the efficient separation and recovery of methanol from waste gases loaded with methanol is proposed, wherein the invention also can be used in an integrated flow chart for the production and processing of methanol. The methanol fractions separated from the waste gases are recovered within the already existing, distillative processing of the crude methanol to pure methanol, so that no separate apparatuses are required for the recovery of the methanol from the loaded scrubber waste waters. The valuable substance methanol is recovered and the impact on the environment is reduced. By particular aspects of the invention the total (Continued)

degree of methanol separation can be adapted according to the locally applicable emission limit values.

7 Claims, 5 Drawing Sheets

(51) Int. Cl.
*B01D 53/14* (2006.01)
*B01D 5/00* (2006.01)
*C07C 29/151* (2006.01)
*C07C 31/04* (2006.01)

(52) U.S. Cl.
CPC .......... *C07C 29/1518* (2013.01); *C07C 29/76* (2013.01); *C07C 31/04* (2013.01); *B01D 2252/103* (2013.01); *B01D 2256/10* (2013.01); *B01D 2256/16* (2013.01); *B01D 2257/70* (2013.01); *B01D 2257/704* (2013.01); *B01D 2258/02* (2013.01)

(58) Field of Classification Search
CPC ............ B01D 2256/16; B01D 2257/70; B01D 2257/704; B01D 2258/02; C07C 29/76; C07C 29/1518; C07C 31/04
USPC .................................. 261/150, 151, 158, 159
See application file for complete search history.

(56) References Cited

U.S. PATENT DOCUMENTS

| | | | |
|---|---|---|---|
| 4,326,041 | A | 4/1982 | Bahnisch |
| 5,346,593 | A | 9/1994 | Cialkowski et al. |
| 5,827,901 | A | 10/1998 | Konig et al. |
| 6,258,860 | B1 | 7/2001 | Weedon et al. |
| 6,312,503 | B1 * | 11/2001 | Fike ........................ B01D 47/12 |
| | | | 95/211 |
| 7,025,808 | B2 * | 4/2006 | Huber ...................... B01D 3/14 |
| | | | 95/211 |
| 8,758,493 | B2 * | 6/2014 | Gal ......................... B01D 53/62 |
| | | | 96/290 |
| 9,914,088 | B2 * | 3/2018 | Tanaka ............... B01D 53/1475 |
| 2003/0045756 | A1 * | 3/2003 | Mimura ............. B01D 53/1475 |
| | | | 564/498 |
| 2012/0304859 | A1 | 12/2012 | Mihailowitsch et al. |
| 2014/0013945 | A1 * | 1/2014 | Tanaka ............... B01D 53/1418 |
| | | | 95/186 |
| 2015/0241059 | A1 * | 8/2015 | Oishi ..................... F23J 15/006 |
| | | | 423/220 |

FOREIGN PATENT DOCUMENTS

| | | |
|---|---|---|
| EP | 0478889 A2 | 4/1992 |
| EP | 0790226 A1 | 8/1997 |
| EP | 0802893 A1 | 10/1997 |
| EP | 1016643 A1 | 7/2000 |
| EP | 2168938 A1 | 3/2010 |

* cited by examiner

PROCESS FOR THE SEPARATION OF METHANOL FROM GAS MIXTURES

CROSS REFERENCE TO RELATED APPLICATIONS

This application is a § 371 of International PCT Application PCT/EP2016/025170, filed Dec. 6, 2016, which claims the benefit of EP15400056.6, filed Dec. 18, 2015, both of which are herein incorporated by reference in their entireties.

FIELD OF THE INVENTION

The present invention relates to a washing apparatus for the separation of methanol from gases, in particular from process waste gases of the synthesis and further processing of methanol, by water washing. Furthermore, the invention comprises a process for the separation and recovery of methanol from gases by water washing with the washing apparatus.

BACKGROUND OF THE INVENTION

Processes for the production of methanol by catalytic conversion of synthesis gas containing hydrogen and carbon oxides have long since been known to those skilled in the art. For example, in Ullmann's Encyclopedia of Industrial Chemistry, Sixth Edition, 1998 Electronic Release, Chapter "Methanol", Sub-chapter 5.2 "Synthesis", various basic processes for the production of methanol are described.

A more advanced, two-stage process for the production of methanol is known for example from EP 0 790 226 B1. The methanol is produced in a cyclic process in which a mixture of fresh and partly reacted synthesis gas first is supplied to a water-cooled reactor and then to a gas-cooled reactor, in each of which the synthesis gas is converted to methanol on a copper-based catalyst. The methanol produced in the process is separated from the synthesis gas to be recirculated, which then is countercurrently guided through the gas-cooled reactor as coolant and preheated to a temperature of 220 to 280° C., before it is introduced into the first synthesis reactor. A part of the synthesis gas to be recirculated is removed from the process as purge stream (so-called purge), which is small as compared to the gas inventory present in the system, in order to prevent that inert components, impurities or by-products accumulate within the synthesis loop. This measure is also taught in the unexamined German Patent Application DE 2934332 A1 and in the European Patent Application EP 1016643 A1.

The purge gas stream discharged from the synthesis loop still is loaded with significant fractions of methanol. The same applies for other waste gas streams which are obtained within the methanol synthesis and the processing of the raw products, such as for example waste gases from methanol expansion tanks or waste gases from storage tanks for crude methanol, methanol-water mixtures or pure methanol. Crude methanol is understood to be the primary product originating directly from the methanol synthesis before the distillative processing to pure methanol.

Methanol storage tanks frequently are designed as fixed-roof tanks, wherein for inertization of the inner volume not filled with methanol the same frequently is rinsed or filled with nitrogen. The nitrogen atmosphere thereby is saturated with methanol. When loading the tanks or due to tank breathing, for example due to solar radiation, nitrogen loaded with methanol is discharged from the tank, in order to avoid an overpressure in the tank.

The methanol fractions of such waste gases are quite significant due to the low boiling point of the methanol of 65° C. at ambient pressure, as the waste gases generally are saturated with methanol vapor at the respective temperature. For example, under saturation conditions the methanol concentration in a waste gas stream with a temperature of 42° C. roughly is 33 vol-%.

In view of these methanol contents it is plausible that the recovery of the methanol from the waste gases provides an important contribution to the economy of the methanol synthesis process. Against the background of the high toxicity of the methanol, on the other hand, it is not justifiable either for reasons of environmental protection to emit waste gases with such high methanol contents to the environment without after treatment. Finally, high methanol contents in waste gases also create problems during their further processing, as methanol can condense out and thus for example damage gas burners.

Due to the high water solubility of the methanol, washing of the waste gases with water as washing agent has proved its worth as separation method. The disclosed European Patent Application EP 2 168 938 A1 for example teaches the recovery of methanol from waste gases of the crude methanol distillation by water washing in a countercurrent column. The European patent specification EP 0 802 893 B1 also describes the separation and recovery of methanol from waste gases of the crude methanol distillation by water washing.

The U.S. Pat. No. 5,346,593 A describes a distillation column for obtaining crude methanol, which at its head is equipped with a water washing stage and serves for the separation of methanol residues from a waste gas stream leaving the column.

Finally, the European patent specification EP 0 009 385 B1 discloses the separation of methanol from the purge gas stream discharged from the synthesis loop by means of water washing and the recovery of the separated methanol by means of distillation.

When using water as washing agent in the separation of methanol from gases, it is advantageous that methanol readily dissolves in water. The heat quantity released during the condensation and the absorption of the methanol, however, impairs the solubility of the methanol in water and thus the separation efficiency. Therefore, a need exists for washing apparatuses which take account of this fact.

SUMMARY OF THE INVENTION

Against this background it is the object of the present invention to provide a washing apparatus and a process for its application, in which and by which an efficient recovery of methanol from gases, in particular from process waste gases of the synthesis, storage and further processing of methanol, is ensured.

This object is solved by a process and by a washing apparatus with the features as described herein.

Washing Apparatus According to an Embodiment of the Invention:

A washing apparatus for the separation of methanol from gases by water washing, comprising the following components and assemblies:

(a) a washing column, comprising a jacket which—based on a properly arranged condition of the washing column—extends along a longitudinal axis extending parallel to the vertical and which encloses an interior space of the washing column, wherein the interior space is divided into an upper and a lower region, which each comprise at least one mass transfer zone and which are separated from each other by means of a separation tray, in particular a chimney tray, wherein the tray is permeable for a gas flow directed from the lower to the upper mass transfer zone, but is impermeable for a liquid flow directed from the upper to the lower mass transfer zone and is suitable to temporarily store a defined volume of washing agent flowing out of the upper mass transfer zone, wherein the upper and the lower mass transfer zone are equipped with mass transfer devices, preferably separation trays, sieve trays, bubble trays, valve trays, structured packings or packed beds or combinations of these mass transfer devices, (b) a first heat exchanger, a conduit for supplying water as washing agent to the first heat exchanger, a conduit for discharging a cooled stream of washing agent from the first heat exchanger and for supplying the cooled stream of washing agent into the upper region of the washing column, wherein the addition point is arranged above the upper mass transfer zone and is designed as liquid distributor, (c) a second heat exchanger, a conduit for discharging a stream of washing agent partly loaded with methanol from the separation tray and for supplying the stream of washing agent partly loaded with methanol to the second heat exchanger, a conduit for discharging the cooled stream of washing agent partly loaded with methanol from the second heat exchanger and for supplying the cooled stream of washing agent partly loaded with methanol into the lower region of the washing column, wherein the addition point is arranged below the chimney tray and above the lower mass transfer zone and is designed as liquid distributor, (d) a conduit for discharging a stream of washing agent loaded with methanol from the lower region of the washing column as its bottom product, wherein the withdrawal point of the loaded stream of washing agent is arranged below the lower mass transfer zone, (d) a conduit for supplying a gas stream loaded with methanol into the lower region of the washing column, wherein the addition point is arranged below the lower mass transfer zone, (f) a conduit for discharging a gas stream reduced in its methanol loading from the upper region of the washing column as its top product, wherein the withdrawal point of the gas stream is arranged above the upper mass transfer zone.

Process According to an Embodiment of the Invention:

A process for the separation and recovery of methanol from gases by water washing, comprising the following steps:

(a) providing a washing column, comprising a jacket which—based on a properly arranged condition of the washing column—extends along a longitudinal axis extending parallel to the vertical and which encloses an interior space of the washing column, wherein the interior space is divided into an upper and a lower region, which each comprise at least one mass transfer zone and which are separated from each other by means of a tray, in particular a chimney tray, wherein the tray is permeable for a gas flow directed from the lower to the upper mass transfer zone, but is impermeable for a liquid flow directed from the upper to the lower mass transfer zone and is suitable to temporarily store a defined volume of washing agent flowing out of the upper mass transfer zone, wherein the upper and the lower mass transfer zone are equipped with mass transfer devices, preferably separation trays, sieve trays, bubble trays, valve trays, structured packings or packed beds or combinations of these mass transfer devices, (b) supplying water as washing agent to a first heat exchanger, cooling the washing agent in the first heat exchanger, discharging a cooled stream of washing agent from the first heat exchanger and supplying the cooled stream of washing agent into the upper region of the washing column, wherein the addition point is arranged above the upper mass transfer zone and is designed as liquid distributor, (c) discharging a stream of washing agent partly loaded with methanol from the separation tray and supplying the stream of washing agent partly loaded with methanol to the second heat exchanger, discharging the cooled stream of washing agent partly loaded with methanol from the second heat exchanger and supplying the cooled stream of washing agent partly loaded with methanol into the lower region of the washing column, wherein the addition point is arranged below the chimney tray and above the lower mass transfer zone and is designed as liquid distributor, (d) discharging a stream of washing agent loaded with methanol from the lower region of the washing column as its bottom product, wherein the withdrawal point of the loaded stream of washing agent is arranged below the lower mass transfer zone, (e) supplying a gas stream loaded with methanol into the lower region of the washing column, wherein the addition point is arranged below the lower mass transfer zone, (f) discharging a gas stream reduced in its methanol loading from the upper region of the washing column as its top product, wherein the withdrawal point of the gas stream is arranged above the upper mass transfer zone.

The water used as washing agent mostly is demineralized water. However, other water qualities, in particular those of higher purity, for example high-purity water or distilled water, can also be used as washing agent. Water of lower purity can be used as washing agent when the accompanying substances present create no problems in downstream process stages. When using the washing apparatus according to the invention within a plant for the synthesis of crude methanol and its purification to pure methanol, it is possible to also use water streams already partly loaded with methanol as washing agent, when the product specifications of the pure methanol product are complied with nevertheless.

PREFERRED ASPECTS OF THE INVENTION

In a preferred aspect of the invention the washing apparatus furthermore comprises a conduit for the recirculation of at least a part of the bottom product of the washing column to the second heat exchanger, wherein the recirculated part of the bottom product of the washing column is combined with the stream of washing agent partly loaded with methanol. The throughput of cooled washing agent in the lower region of the washing column and thus the methanol separation rate thereby is increased.

In a further preferred aspect of the invention the washing apparatus furthermore comprises a condensation apparatus arranged in the upper region of the interior space, above the upper mass transfer zone and above the upper liquid distributor, preferably a reflux condenser.

The total separation rate of the methanol in the washing apparatus thereby is increased once again.

In a preferred aspect of the process according to the invention at least a part of the bottom product of the washing column is recirculated to the second heat exchanger and combined with the stream of washing agent partly loaded with methanol. The throughput of the washing agent in the lower region of the washing column and thus the methanol separation rate thereby is increased.

In a further preferred aspect of the process according to the invention combining the bottom product of the washing column with the stream of washing agent partly loaded with methanol is effected before supplying the same to the second heat exchanger. By cooling the combined stream of washing agent, the methanol separation rate is increased again.

In a further aspect of the process according to the invention a condensation of liquid out of the gas stream leaving the upper mass transfer zone is effected by means of a condensation apparatus arranged in the upper region of the interior space, above the upper mass transfer zone and above the upper liquid distributor, preferably a reflux condenser. The total separation rate of the methanol in the washing apparatus thereby is increased once again.

Preferably, the process according to the invention is used for the separation and recovery of methanol from waste gases of methanol storage tanks or from waste gases of methanol expansion tanks or from purge gas of the methanol synthesis or from combinations of these waste gases. All said waste gases contain significant amounts of methanol in vapor form, so that the separation and recovery of this substance is expedient for economic and ecological reasons.

In a preferred aspect of the process according to the invention demineralized water is used as washing agent. In integrated production plants it mostly is available as operating material and has particularly good absorption properties for methanol.

The methanol-water mixture obtained as bottom product of the washing column preferably is supplied to a methanol expansion tank, a methanol storage tank or a distillation apparatus for obtaining pure methanol.

BRIEF DESCRIPTION OF THE DRAWINGS

Further features, advantages and possible applications of the invention can also be taken from the following description of exemplary embodiments and numerical examples as well as the drawings. All features described and/or illustrated form the subject-matter of the invention per se or in any combination, independent of their inclusion in the claims or their back-reference.

In the drawings.

DETAILED DESCRIPTION OF THE INVENTION

Figure 1:
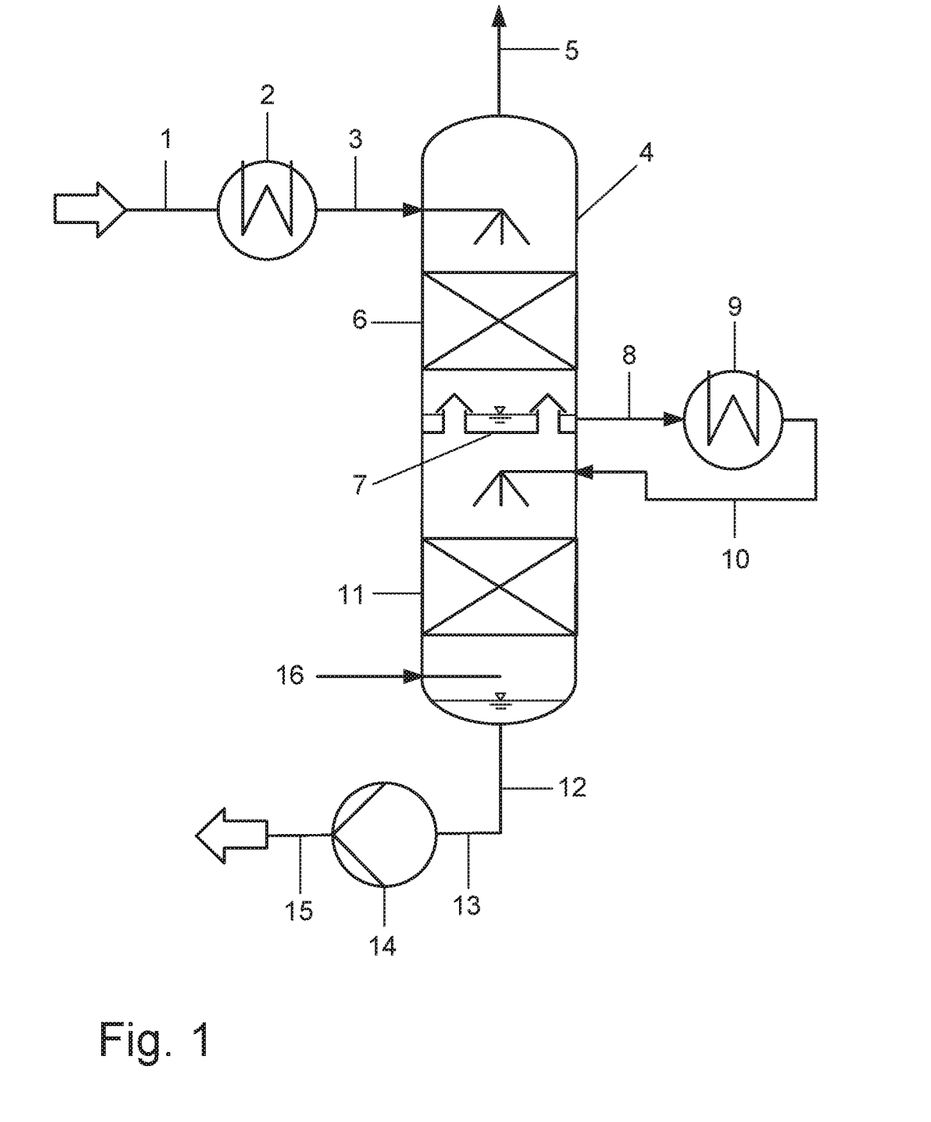
FIG. 1 shows the schematic representation of the process according to the invention and the washing apparatus according to the invention in a first aspect.

The process of the invention and the washing apparatus of the invention according to a first aspect are explained in FIG. 1. Via conduit 1, demineralized water is guided to the heat exchanger 2 as washing agent and is cooled there by indirect heat exchange against cooling water. Via conduit 3, the cooled washing agent is guided to the washing column 4 and charged to the same through a distribution device schematically indicated in the Figure. By means of gravity, the washing agent then flows through the upper mass transfer zone 6, which is a packed bed. In the upper mass transfer zone 6, an intensive contact between the washing agent and the gas stream loaded with methanol, which is to be purified, is made due to the high specific surface of the packed bed. During the absorption of the methanol in the washing agent, the solution enthalpy is released and the washing agent is heated correspondingly.

After leaving the upper mass transfer zone 6, the washing agent now partly loaded with methanol gets to the separation tray 7 which is designed as chimney tray. The separation tray is permeable for the gas stream passing over from the lower into the upper region of the column interior, but is impermeable for the washing agent flowing out of the upper mass transfer zone, whereby the latter accumulates on the separation tray. The level of the washing agent on the separation tray is determined by the height of the chimneys.

By means of conduit 8, a part of the washing agent partly loaded with methanol, which has accumulated on the separation tray 7, is continuously withdrawn from the washing column by means of a non-illustrated conveying device, guided to the heat exchanger 9 and cooled there by indirect heat exchange against cooling water. The solution enthalpy previously transmitted to the washing agent during the adsorption of the methanol here again is at least partly dissipated from the same.

Since the stream of washing agent withdrawn from the washing column via conduit 8 must correspond to the stream of washing agent flowing out of the upper mass transfer zone, in order to ensure a constant liquid level on the separation tray, the heat exchanger 9 must be designed with regard to its heat-exchange surface and/or the used coolant temperature, in order to achieve a desired temperature decrease of the washing agent.

Withdrawing the washing agent partly loaded with methanol, which has accumulated on the separation tray 7, from the washing column can be effected purely by means of gravity also without conveying device, when this is permitted by the pressure loss in the conduits 8 and 10, the heat exchanger 9 and the distribution device. In this case, a corresponding control device, for example a control valve, is to be provided.

Via conduit 10, the cooled washing agent is guided back to the washing column 4 and charged to the same through a distribution device schematically indicated in the Figure. By means of gravity, the washing agent then flows through the lower mass transfer zone 11, which again is a packed bed. In the lower mass transfer zone 11, an intensive contact between the washing agent and the gas stream loaded with methanol, which is to be purified, is made due to the high specific surface of the packed bed and thus further methanol is absorbed in the washing agent.

In the sense of the invention, other mass transfer devices, preferably separation trays, sieve trays, bubble trays, valve trays or structured packings can also be used in the upper mass transfer zone 6 and in the lower mass transfer zone 11. Combinations of said mass transfer devices also are possible, with the mass transfer zones then being divided into corresponding sections which each are equipped with one of said mass transfer devices.

The washing agent loaded with methanol accumulates in the lower region of the washing column as column sump. It is discharged from the same via the conduits 12 and 13, the pump 14 and the conduit 15 and supplied to the storage, processing or some other use.

Via conduit 16, the gas stream to be purified is charged to the washing column 4 at its lower end, between column sump and lower mass transfer zone. In counterflow to the washing agent it then first flows through the lower mass transfer zone, in which a pre-separation of the methanol is effected by absorption in the washing agent. Subsequently, the gas stream to be purified flows through the separation tray and the upper mass transfer zone, in which a fine separation of the residual methanol is effected up to traces. The gas stream now purified is discharged via conduit 5 and released to the environment or supplied to a further processing.

In the present example, the gas stream to be purified is a waste gas stream from methanol storage tanks. Inert gas, frequently nitrogen, is used therein as purge gas or cover gas, in order to avoid an air contact of the stored methanol. The inert gas thereby is enriched with significant amounts of methanol.

The washing apparatus according to the invention or the separation process according to the invention likewise can be used for the separation of methanol from waste gases of methanol expansion tanks or from purge gas of the methanol synthesis or from combinations of the aforementioned waste gases.

Figure 2:
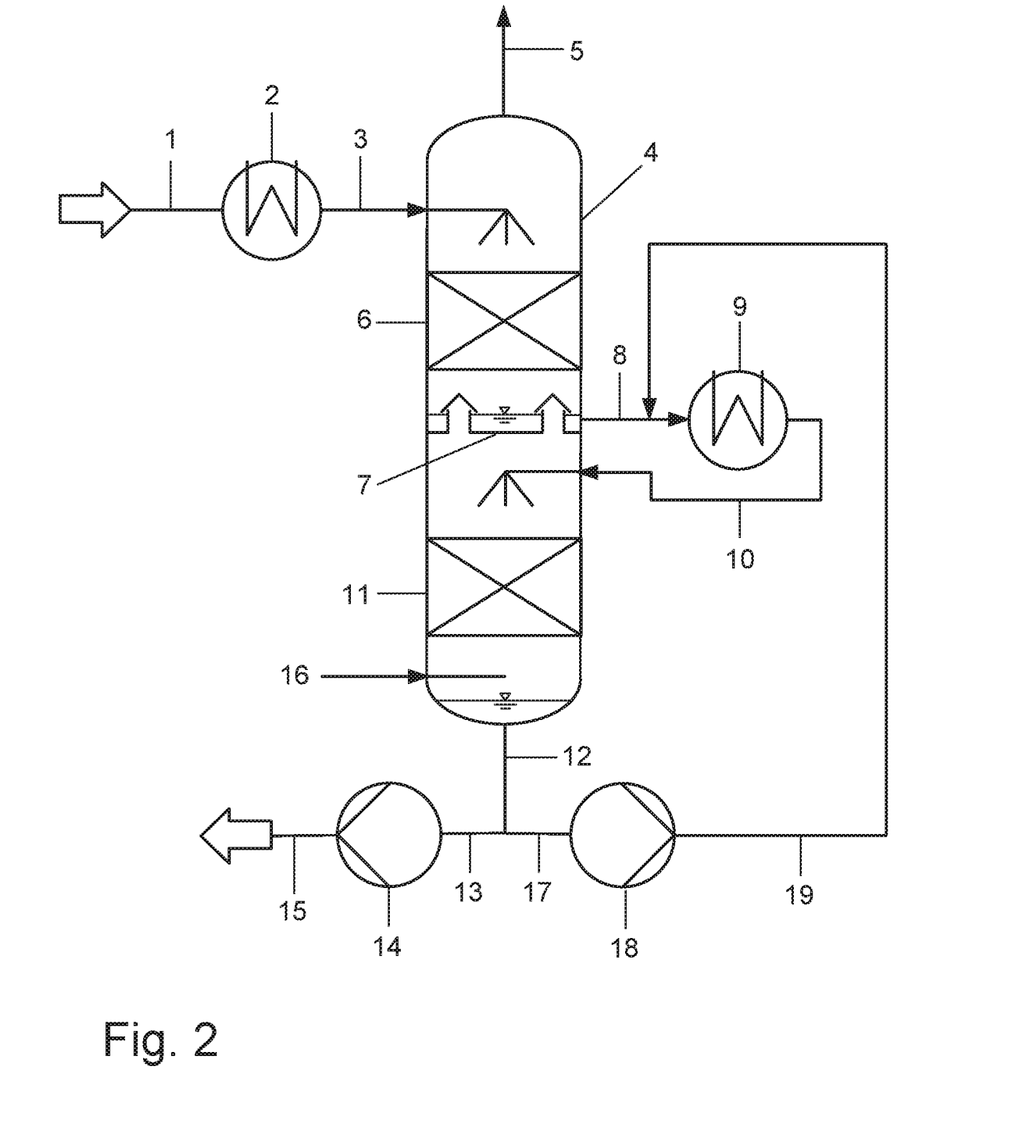
FIG. 2 shows the schematic representation of the process according to the invention and the washing apparatus according to the invention in a second aspect.

In the second aspect of the process according to the invention or the washing apparatus according to the invention as shown in FIG. 2, in addition to the embodiment shown in FIG. 1, a part of the washing agent loaded with methanol, which is discharged from the column sump, is recirculated to the heat exchanger 9 via conduit 17, pump 18 and conduit 19 and charged to said heat exchanger together with the washing agent discharged from the washing column 4 via conduit 8. In this way, the throughput of the washing agent in the lower region of the washing column and thus the methanol separation rate is increased. By cooling the combined stream of washing agent from conduits 8 and 19, the methanol separation rate even is increased further.

Figure 3:
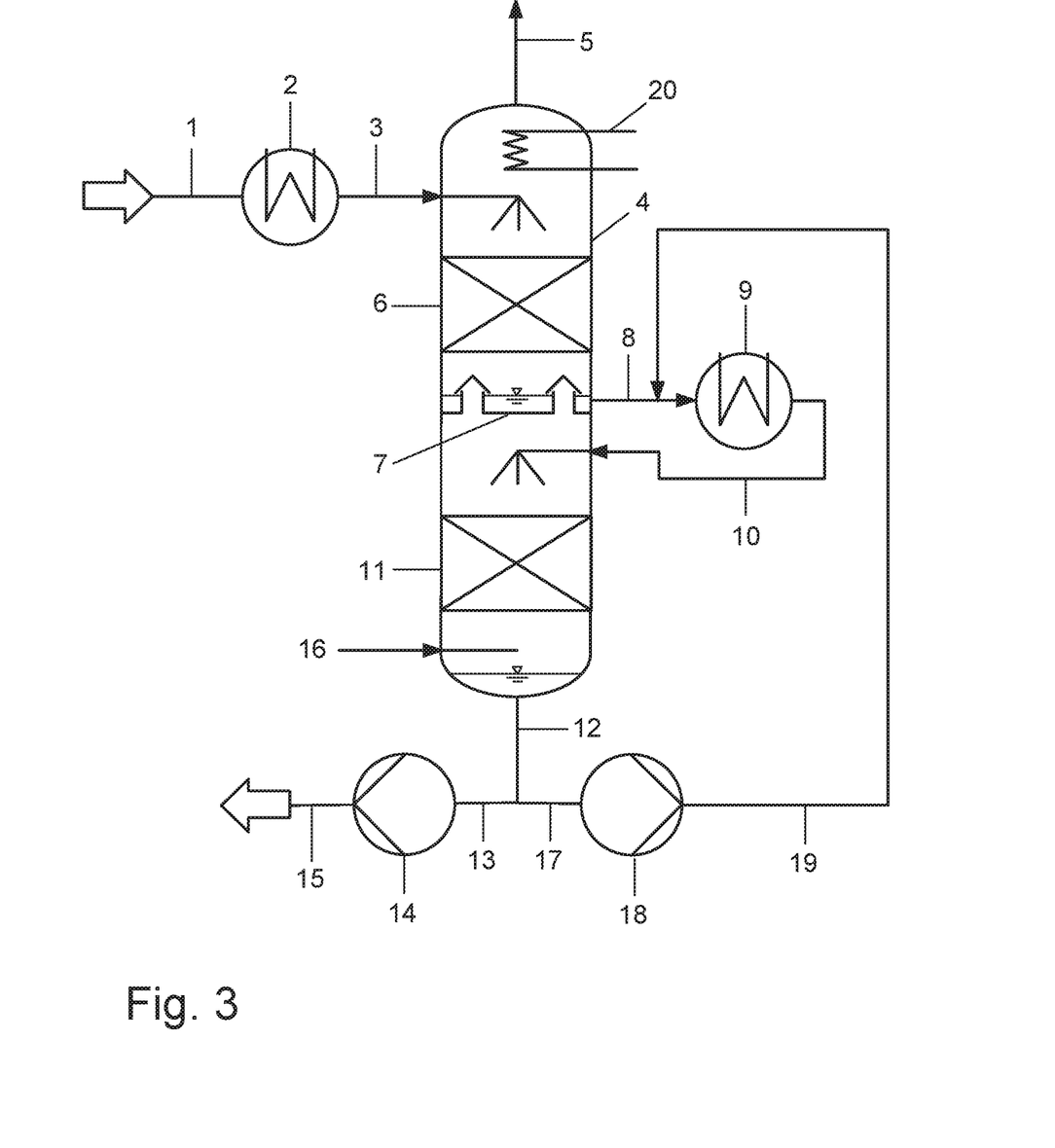
FIG. 3 shows the schematic representation of the process according to the invention and the washing apparatus according to the invention in a third aspect.

In the third aspect of the process according to the invention and the washing apparatus according to the invention as shown in FIG. 3, the washing column 4 as a supplement to the embodiment shown in FIG. 2 is equipped with an additional condensation apparatus, preferably a reflux condenser, arranged in the upper region of the interior space, above the upper mass transfer zone and above the upper liquid distributor. The total separation rate of the methanol in the washing apparatus thereby is increased once again and the gas stream discharged via conduit 5 is liberated from the last methanol residues. The use of the condensation apparatus also is possible in the aspect of the invention as shown in FIG. 1, i.e. without recirculation of loaded washing agent via conduit 19. The total separation rate of the methanol is slightly lower than in the aspect shown in FIG. 3.

Figure 4:
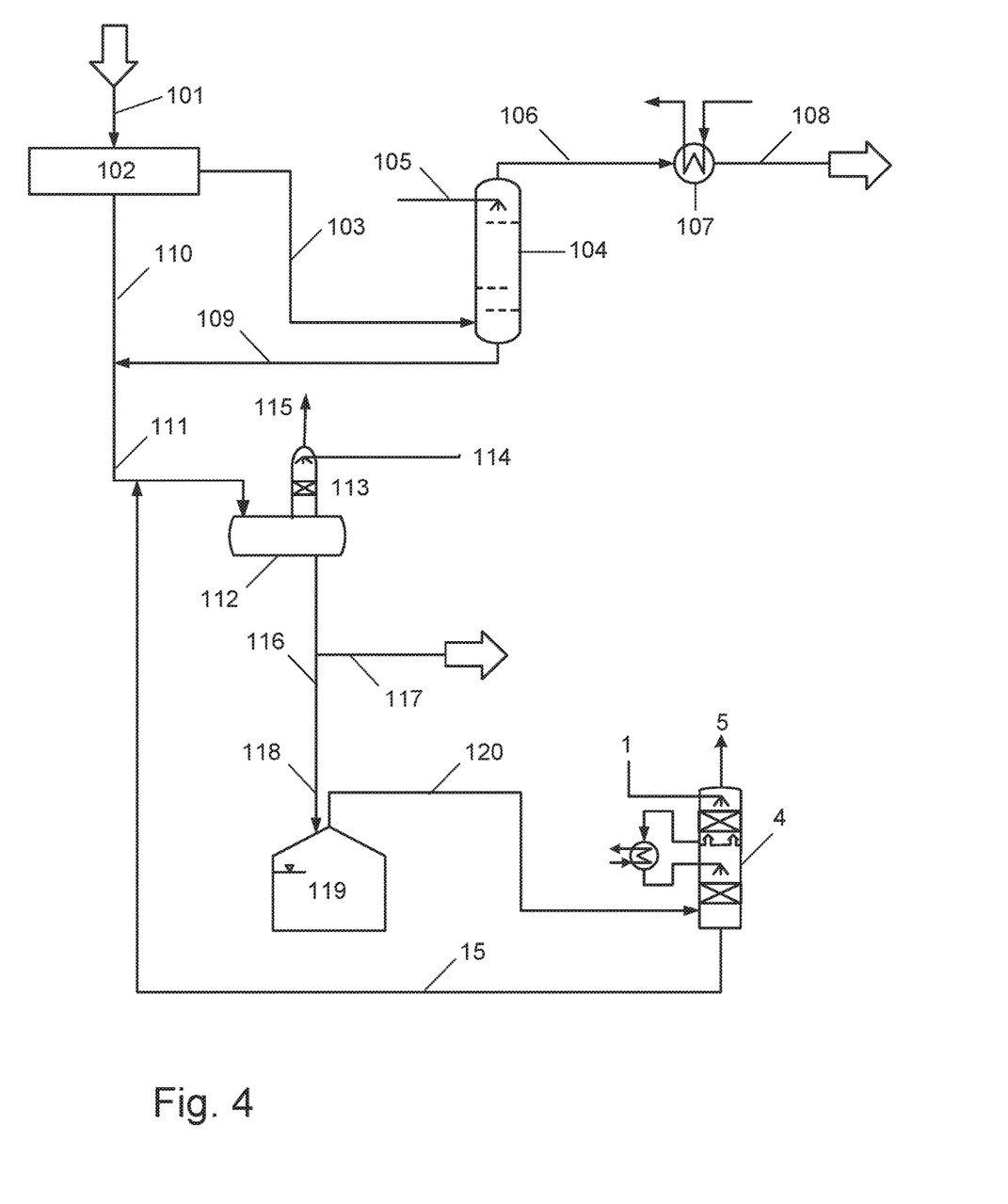
FIG. 4 shows the integration of the washing apparatus according to the invention in a flow chart for the processing and storage of crude methanol from the methanol synthesis.

FIG. 4 shows the integration of the washing apparatus according to the invention in a flow chart for the processing and storage of crude methanol from the methanol synthesis.

Via conduit 101 synthesis gas consisting of hydrogen and carbon oxides is introduced into the methanol synthesis reactor 102 which here is shown only schematically and is not explained in detail, in which the synthesis gas is partly converted to methanol under the conditions of methanol synthesis. The crude methanol produced in the process is discharged from the methanol synthesis reactor via conduit 110.

The largest part of the synthesis gas not converted during the methanol synthesis is recirculated to the inlet of the methanol synthesis reactor via a non-illustrated synthesis gas circuit. Via conduit 103, the remaining fraction of the non-converted synthesis gas is discharged from the methanol synthesis reactor as purge gas or flushing gas and guided to the purge gas washing apparatus 104. This is a washing column known per se, which can be equipped with trays, packed beds or structured packings, in order to intensify the mass transfer between gas and liquid. The purge gas stream is charged to the purge gas washing apparatus at its bottom side and is countercurrently brought in contact with a water stream supplied as washing agent via conduit 105, whereby its content of methanol vapor is reduced. In the present exemplary embodiment and in those described below, demineralized water is used as washing agent—unless otherwise noted.

The purge gas depleted of methanol leaves the purge gas washing apparatus via conduit 106. It can then optionally be heated in the heat exchanger 107 by indirect heat exchange against low-pressure steam as heating medium and via conduit 108 be discharged from the process and be guided to a non-illustrated hydrogen recovery system.

The water loaded with methanol in the purge gas washing apparatus is discharged from the same via conduit 109 and together with the crude methanol supplied via conduit 110 guided to the expansion tank 112 via conduit 111. The mixture of crude methanol and water is depressurized in said expansion tank from 7.0 MPa,g to a pressure of 0.5 MPa,g (g designates the corresponding pressure unit at overpressure). In the expansion gas washing apparatus 113 constructionally connected with the expansion tank and in fluid connection with the same the gases or vapors released during the depressurization are brought in contact with a water stream supplied as washing agent via conduit 114, whereby its content of methanol vapor is reduced. The expansion gas washing apparatus also is a washing column known per se, which can be equipped with trays, packed beds or structured packings, in order to intensify the mass transfer between gas and liquid. The expansion gas stream depleted of methanol leaves the expansion gas washing apparatus via conduit 115.

The depressurized mixture of crude methanol and water is discharged from the expansion tank 112 via conduit 116. Via conduit 117 it can completely or partly be guided to a non-illustrated distillation apparatus in which the crude methanol is processed further to pure methanol by distillative separation of water.

Via conduit 118, the fraction of the mixture of crude methanol and water not guided to the distillation apparatus is guided to the tank 119 and introduced into the same. At a later time, crude methanol can be withdrawn from the tank and be supplied to the distillative processing. The tank 119 is a fixed-roof tank in which the free inner volume of the tank is filled by nitrogen, which is supplied via a non-illustrated conduit, and thus is inertized. The nitrogen atmosphere thereby is saturated with methanol. When loading the tanks or due to tank breathing, for example due to solar radiation, nitrogen loaded with methanol is discharged from the tank via conduit 120, in order to avoid an overpressure in the tank. This inertizing gas stream loaded with methanol vapor is guided to the gas washing apparatus 4, charged to the same on its bottom side, and is countercurrently brought in contact with a water stream supplied as washing agent via conduit 1, whereby its content of methanol vapor is reduced.

Via conduit 15, the washing agent loaded with methanol is discharged from the inertizing gas washing apparatus and guided to the expansion tank 12 via conduit 111. If distinctly different pressures exist in the conduits 15 and 111, the washing agent loaded with methanol also can be guided to the expansion tank separate from conduit 111.

Figure 5:
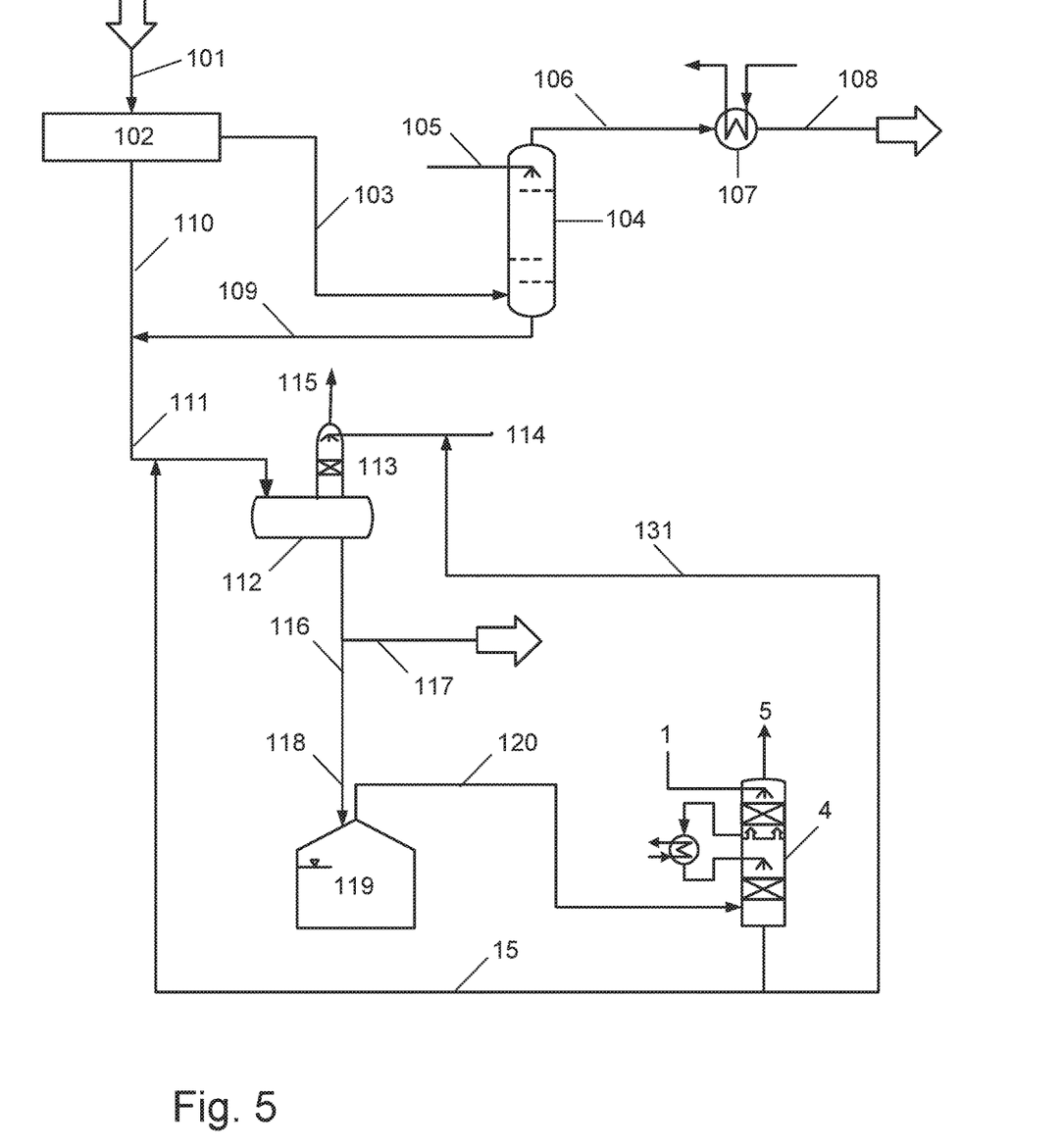
FIG. 5 shows the integration of the washing apparatus according to the invention in a flow chart for the processing and storage of crude methanol from the methanol synthesis in a further aspect.

FIG. 5 shows the integration of the washing apparatus according to the invention in a flow chart for the processing and storage of crude methanol from the methanol synthesis in a further aspect.

The process according to the invention and the apparatus according to the invention correspond to the aspect shown in FIG. 4 up to the plant component 120. Now, however, conduit 131 is added, with which at least a part of the washing agent discharged from the washing apparatus via conduit 15 is guided to the expansion gas washing apparatus 113 via conduit 114. Due to the aspect of the invention as shown in FIG. 5, a particularly large fraction of the demineralized water used as washing agent in the expansion gas washing apparatus can be replaced by streams of water loaded with methanol from the washing apparatus 4.

In FIGS. 4 and 5 the washing apparatus each is indicated only schematically. It should therefore be noted that in its integration into a flow chart for the processing and storage of crude methanol from the methanol synthesis various configurations of the washing apparatus can be used, in particular also the configurations shown in FIG. 1, FIG. 2 and FIG. 3.

Numerical Examples

In the following numerical example, the separation of methanol from the inertizing waste gas of a methanol tank farm was considered. The nitrogen-based inertizing gas was saturated with methanol at 42° C. The volume flow of the waste gas each was 100000 SCFH, corresponding to 2831.68 m$^3$/h. The composition of the inertizing waste gas was as follows:

Nitrogen: 66.75, water: 0.008 vol-%, methanol: 33.17 vol-%, methyl ethyl ketone (MEK): 2.4 vol-ppm, ethanol: 1.2 vol-ppm, 2-propanol: 0.3 vol-ppm In all cases described below, demineralized water with a mass flow of 2900 kg/h and a temperature of 40° C. was used as fresh washing agent. The washing column used each had the same number of theoretical trays and was equipped with a chimney tray as separation tray. As cooling medium, demineralized water with 25 wt-% of monoethylene glycol was each used as anti-freeze agent, wherein the forward flow temperature each was 5° C. and the return flow temperature each was 15° C.

In the following Table, numerical examples are listed for the aspects of the invention as shown in FIG. 1, FIG. 2 and FIG. 3.

As can be taken from the Table, the total degree of methanol separation is more than 99% in all three aspects of the invention. The aspect according to FIG. 3 has the highest total degree of methanol separation in the amount of 99.98%. The total consumption of cooling agent even is slightly reduced as compared to the aspect according to FIG. 2.

| Configuration | | FIG. 1 without recirculation conduit 19 | FIG. 2 with recirculation conduit 19 | FIG. 3 with recirculation conduit 19 and condenser 20 |
|---|---|---|---|---|
| Inertizing waste gas | | | | |
| Methanol mass flow | kg/h | 1270.6 | 1270.6 | 1270.6 |
| Composition: | | | | |
| Nitrogen | vol-% | | 66.75 | |
| Water | vol-% | | 0.008 | |
| Methanol | vol-% | | 33.17 | |
| MEK | vol-ppm | | 2.4 | |
| Ethanol | vol-ppm | | 1.2 | |
| 2-Propanol | vol-ppm | | 0.3 | |
| Volume flow | SCFH | | 100.000 | |
| Temperature | ° C. | | 42.0 | |
| Purified waste gas | | | | |
| Temperature | ° C. | 52.2 | 20.5 | 15.0 |
| Methanol mass flow | kg/h | 10.8121 | 0.4087 | 0.2434 |
| Composition: | | | | |
| Nitrogen | vol-% | 86.27 | 97.64 | 98.33 |
| Water | vol-% | 13.37 | 2.35 | 1.66 |
| Methanol | vol-ppm | 3649 | 156.1 | 93.6 |
| MEK | vol-ppm | 3.1 | 3.5 | 3.5 |
| Ethanol | vol-ppm | 1.5 | 1.5 | 1.5 |
| 2-Propanol | vol-ppm | 0.3 | 0.4 | 0.4 |
| Total degree of methanol separation | % | 99.15% | 99.97% | 99.98% |
| Mass flow conduit 19 | kg/h | 0 | 8500 | 3600 |
| Coolant consumption (Ref. Num.) | | | | |
| 2 | kg/h | 8236 | 8236 | 8236 |
| 9 | kg/h | 13175 | 34866 | 28131 |
| 20 | kg/h | 0 | 0 | 6653 |
| Total | kg/h | 21411 | 43102 | 43020 |
| Heat exchanger (Ref. Num.) U*A | | | | |
| 2 | W/° C. | 6580 | 6580 | 6580 |
| 9 | W/° C. | 8260 | 26400 | 17800 |
| 20 | W/° C. | 0 | 0 | 5540 |
| Total | W/° C. | 14840 | 32980 | 29920 |

INDUSTRIAL APPLICABILITY

With the invention a washing apparatus and a process for the efficient separation and recovery of methanol from waste gases loaded with methanol is proposed, wherein the invention also can be used in an integrated flow chart for the production and processing of methanol. The methanol fractions separated from the waste gases are recovered within the already existing, distillative processing of the crude methanol to pure methanol, so that no separate apparatuses are required for the recovery of the methanol from the loaded scrubber waste waters. The valuable substance methanol is recovered and the impact on the environment is reduced. By particular aspects of the invention the total degree of methanol separation can be adapted according to the locally applicable emission limit values.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A process for the separation and recovery of methanol from gases by water washing, the process comprising the following steps:
    a) providing a washing column, comprising a jacket, during operation of the washing column, extends along a longitudinal axis extending parallel to the vertical and which encloses an interior space of the washing column, wherein the interior space is divided into an upper and a lower region, which each comprise at least one mass transfer zone and which are separated from each other by means of a tray, wherein the tray is permeable for a gas flow directed from the lower to the upper mass transfer zone, but is impermeable for a liquid flow directed from the upper to the lower mass transfer zone and is suitable to temporarily store a defined volume of a washing agent flowing out of the upper mass transfer zone, wherein the upper and the lower mass transfer zone are equipped with mass transfer devices;
    b) supplying water as the washing agent to a first heat exchanger, cooling the washing agent in the first heat exchanger, discharging a cooled stream of washing agent from the first heat exchanger and supplying the cooled stream of washing agent into the upper region of the washing column, wherein the addition point is arranged above the upper mass transfer zone and is designed as a liquid distributor;
    c) discharging a stream of washing agent partly loaded with methanol from the separation tray and supplying the stream of washing agent partly loaded with methanol to a second heat exchanger, discharging the cooled stream of washing agent partly loaded with methanol from the second heat exchanger and supplying the cooled stream of washing agent partly loaded with methanol into the lower region of the washing column, wherein the addition point is arranged below the tray and above the lower mass transfer zone and is designed as a liquid distributor;
    d) discharging a stream of washing agent loaded with methanol from the lower region of the washing column as its bottom product, wherein the withdrawal point of the loaded stream of washing agent is arranged below the lower mass transfer zone;
    e) supplying a gas stream loaded with methanol into the lower region of the washing column, wherein the addition point is arranged below the lower mass transfer zone; and
    f) discharging a gas stream reduced in its methanol loading from the upper region of the washing column as its top product, wherein the withdrawal point of the gas stream is arranged above the upper mass transfer zone.

2. The process according to claim 1, wherein at least a part of the bottom product of the washing column is recirculated to the second heat exchanger and combined with the stream of washing agent partly loaded with methanol.

3. The process according to claim 2, wherein combining the bottom product of the washing column with the stream of washing agent partly loaded with methanol is effected before supplying the same to the second heat exchanger.

4. The process according to claim 1, wherein a condensation of liquid out of the gas stream leaving the upper mass transfer zone is effected by means of a condensation apparatus arranged in the upper region of the interior space, above the upper mass transfer zone and above the upper liquid distributor.

5. The process according to claim 1, wherein demineralized water is used as washing agent.

6. The process according to claim 1, wherein the bottom product of the washing column is supplied to a methanol expansion tank, a methanol storage tank or a distillation apparatus for obtaining pure methanol.

7. The process according to claim 1, wherein the mass transfer devices are selected from the group consisting of separation trays, sieve trays, bubble trays, valve trays, structured packings, packed beds, and combinations thereof.

* * * * *